(12) United States Patent
Sadhasivam

(10) Patent No.: US 9,763,572 B2
(45) Date of Patent: Sep. 19, 2017

(54) QUANTITATIVE PUPILLOMETRY AS A BEDSIDE PREDICTOR OF POSTOPERATIVE RESPIRATORY DEPRESSION

(71) Applicant: Children's Hospital Medical Center, Cincinnati, OH (US)

(72) Inventor: Senthilkumar Sadhasivam, Mason, OH (US)

(73) Assignee: Children's Hospital Medical Center, Cincinnati, OH (US)

(*) Notice: Subject to any disclaimer, the term of this patent is extended or adjusted under 35 U.S.C. 154(b) by 0 days.

(21) Appl. No.: 15/042,137

(22) Filed: Feb. 11, 2016

(65) Prior Publication Data

US 2016/0235295 A1    Aug. 18, 2016

Related U.S. Application Data

(60) Provisional application No. 62/117,171, filed on Feb. 17, 2015.

(51) Int. Cl.

| A61B 3/10 | (2006.01) |
|---|---|
| A61B 3/14 | (2006.01) |
| A61B 3/02 | (2006.01) |
| A61B 3/00 | (2006.01) |
| A61B 5/00 | (2006.01) |
| A61B 18/18 | (2006.01) |
| A61B 3/11 | (2006.01) |
| A61B 5/08 | (2006.01) |

(52) U.S. Cl.
CPC ............ *A61B 3/112* (2013.01); *A61B 3/0008* (2013.01); *A61B 3/14* (2013.01); *A61B 5/7275* (2013.01); *A61B 5/08* (2013.01); *A61B 5/4848* (2013.01); *A61B 2560/0475* (2013.01)

(58) Field of Classification Search
CPC ....... A61B 3/103; A61B 19/22; A61B 18/203; A61B 3/1225; A61B 3/02; A61B 3/1015; A61B 3/113; A61B 3/14; A61B 3/1208; A61B 3/024; A61B 3/032; A61B 5/0002; A61B 5/1455; A61B 5/16; A61B 5/4528; G06K 9/00597; G06F 21/32; A61F 9/008; G01V 1/3808
USPC ....... 351/200, 202, 205, 246, 210, 206, 218, 351/221–223; 382/117; 600/300, 301, 600/318, 310, 558, 587; 606/1, 2, 4; 702/1
See application file for complete search history.

(56) References Cited

U.S. PATENT DOCUMENTS

| 5,187,506 A * | 2/1993 | Carter ................... A61B 3/112 351/205 |
| 5,692,502 A * | 12/1997 | Alpert .................. G06F 19/366 600/300 |
| 2011/0136848 A1 * | 6/2011 | Silverman .......... A61K 31/4748 514/282 |

OTHER PUBLICATIONS

Aman, Michael G., et al., "Plasma Pharmacokinetic Characteristics of Risperidone and Their Relationship to Saliva Concentrations in Children with Psychiatric or Neurodevelopmental Disorders", *Clinical Therapeutics*, (2007) vol. 29, No. 7, pp. 1476-1486.

(Continued)

*Primary Examiner* — Dawayne A Pinkney
(74) *Attorney, Agent, or Firm* — Faegre Baker Daniels LLP

(57) ABSTRACT

A non-invasive bedside tool for monitoring central nervous system effects of opioids. The tool illustratively comprises a quantitative pupillometry system for predicting a probability of at least one opioid-related central effect based on detected pupillary effects.

17 Claims, 7 Drawing Sheets

(56) References Cited

OTHER PUBLICATIONS

Chidambaran, Vidya, M.D., et al., "Risk Predictors of Opioid-Induced Critical Respiratory Events in Children: Naloxone Use as a Quality Measure of Opioid Safety", Wiley Periodicals, Inc., *Pain Medicine* (2014), vol. 15, pp. 2139-2149.

Cohen, Mindy, et al., "Pharmacogenetics in Perioperative Medicine", *Curr Opin Anesthesiol* (2012), vol. 25, No. 4, pp. 419-427.

Fukuda, Tsuyoshi, PhD, et al., "Inosine Monophosphate Dehydrogenase (IMPDH) Activity as a Pharmacodynamic Biomarker of Mycophenolic Acid Effects in Pediatric Kidney Transplant Recipients", *J Clin Pharmacol*, Mar. 2011, vol. 51, No. 3, pp. 309-320.

Fukuda, Tsuyoshi, PhD, et al., "Non-steroidal Anti-Inflammatory Drugs may reduce Enterohepatic Recirculation of Mycophenolic Acid in Patients with Childhood-onset Systemic Lupus Erythematosus", *Ther Drug Monit*, Oct. 2011, vol. 33, No. 5, pp. 658-662.

Fukuda, Tsuyoshi, PhD, et al., "UGT1A9, UGT2B7 and MRP2 genotypes can predict mycophenolic acid pharmacokinetic variability in pediatric kidney transplant recipients", *Ther Drug Monit.*, Dec. 2012, vol. 34, No. 6, pp. 671-679.

Mehta, Parinda et al., High-Dose Weekly AmBisome Antifungal Prophylaxis in Pediatric Patients Undergoing Hematopoietic Stem Cell Transplantation: A Pharmacokinetic Study, *Biology of Blood and Marrow Transplantation*, ASBMT, (2006), vol. 12, pp. 235-240.

Mehta, Parinda et al., "Alternate-Day Micafungin Antifungal Prophylaxis in Pediatric Patients Undergoing Hematopoietic Stem Cell Transplantation: A Pharmacokinetic Study", *Biol Blood Marrow Transplant*, (2010), vol. 16, pp. 1458-1462.

Merhar, Stephanie L. M.D., et al., "Pharmacokinetics of Levetiracetam in Neonates with Seizures", *J Pediatri*, (2011) vol. 159, pp. 152-154.

Mouksassi, M.S., et al., "Clinical Trial Simulations in Pediatric Patients Using Realistic Covariates: Application to Teduglutide, a Glucagon-Like Peptide-2 Analog in Neonates and Infants With Short-Bowel Syndrome", *Clinical Pharmacology & Therapeutics*, Dec. 2009, vol. 86, No. 6, pp. 667-671.

Prausa, S.E., et al., "UGT Genotype May Contribute to Adverse Events Following Medication With Mycophenolate Mofetil in Pediatric Kidney Transplant Recipients", *Clinical Pharmacology & Therapeutics*, May 2009, vol. 85, No. 5, pp. 495-500.

Rasmussen-Torvik, Laura J., et al., "Design and Anticipated Outcomes of the eMERGE-PGx Project: A Multi-Center Pilot for Pre-Emptive Pharmacogenomics in Electronic Health Record Systems", *Clin Pharmacol Ther.*, Oct. 2014, vol. 96, No. 4, pp. 482-489.

Sadhasivam, Senthilkumar, M.D., MPH, "Preventing Opioid-Related Deaths in Children Undergoing Surgery", Wiley Periodicals, Inc., *Pain Medicine* (2012); vol. 3, pp. 982-983.

Sadhasivam, Senthilkumar, M.D., MPH, et al., "Genetics of pain perception, COMT and postoperative pain management in children", *Pharmacogenomics*, (2014), vol. 15, No. 3, pp. 277-284.

Saldaña, Shannon N. et al., "Characteristics of Successful Recruitment in Prospective Pediatric Pharmacogenetic Studies", *Clinical Therapeutics*, vol. 33, No. 12, (2011), pp. 2072-2081.

Vinks, Alexander A., et al., "Important Role of Population Pharmacokinetic/Pharmacodynamic Modeling in Pediatric Therapeutics", *The Journal of Pediatrics*, Sep. 2011, vol. 159, No. 3, pp. 361-363.

Wang, Chenguang, et al., "Developmental Changes in Morphine Clearance Across the Entire Paediatric Age Range are Best Described by a Bodyweight-Dependent Exponent Model", *Clin Drug Investig*, (2013), vol. 33, pp. 523-534.

Chidambaran, Vidya, M.D., et al., "Pharmacogenetics and Anesthetic Drugs", *Current Clinical Pharmacology*, (2012), vol. 7, pp. 78-101.

Sadhasivam, S. et al., "Pharmacogenetics and personalizing perioperative analgesia in children", *The Journal of Pain*, vol. 11, Issue 4, Supplement, Apr. 2010, p. S50.

Aissou, Mourad, et al., Objective Assessment of the Immediate Postoperative Analgesia Using Pupillary Reflex Measurement, Anesthesiology, vol. 116, No. 5, (May 2012), pp. 1006-1012.

Anderson, Brian, J., Why is there no morphine concentration-response curve for acute pain?, Pediatric Anesthesia, vol. 24, (2014) pp. 223-238.

Barvais, L., et al., Effect site concentrations of remifentanil and pupil response to noxious stimulation, British Journal of Anesthesia, vol. 91, No. 3, (2003), pp. 347-352.

Behrends, Matthias, et al., Infrared pupillometry to detect the light reflex during cardiopulmonary resuscitation: A case series, Resuscitation, vol. 83, (2012), pp. 1223-1228.

Bernard, Remy, MORPHIT: an observational study on morphine titration in the postanesthetic care unit in children, Pediatric Anesthesia, vol. 24, (2014), pp. 303-308.

Biavari, Michael J., et al., Predictive Factors for Respiratory Complications After Tonsillectomy and Adenoidectomy in Children, Arch Otolaryngol Head Neck Surg, vol. 123, (1997), pp. 517-521.

Boehmer, Ulrike, et al., Self-Reported vs Administrative Race/Ethnicity Data and Study Results, American Journal of Public Health, vol. 92, No. 9, (Sep. 2002), pp. 1471-1473.

Boev, Angel N., et al., Quantitative pupillometry: normative data in healthy pediatric volunteers, J. Neurosurg Pediatrics, vol. 103 (Dec. 2005), pp. 496-500.

Brouillette, Robert T., Let's Chat about Adenotonsillectomy, The New England Journal of Medicine, vol. 368, No. 25, (Jun. 20, 2013), pp. 2428-2429.

Chidambaran, Vidya, et al., Pediatric Acute and Surgical Pain Management: Recent Advances and Future Perspectives, International Anesthesiology Clinics, vol. 50, No. 4, (2012), pp. 66-82.

Clavijo, Claudia F., et at, A sensitive assay for the quantification of morphine and its active metabolites in human plasma and dried blood spots using high-performance liquid chromatography-tandem mass spectrometry, Anal Bioanal Chem vol. 400, (2001), pp. 715-728.

Constant, I., et al., Reflect pupillary dilatation in response to skin incision and alfentanil in children anaesthetized with sevoflurane: a more sensitive measure of noxious stimulation than the commonly used variables, British Journal of Anaesthesia, vol. 96, No. 5, (2006), pp. 614-619.

Crews, KR. et al., Clinical Pharmacogenetics Implementation Consortium Guidelines for Cytochrome P450 2D6 Genotype and Codeine Therapy: 2014 Update, Nature Publishing Group, vol. 95, No. 4, (Apr. 2014), pp. 375-382.

Duedahl, Tina, et al., A qualitative systematic review of morphine treatment in children with postoperative pain, Pediatric Anesthesia, vol. 17, (2007), pp. 756-774.

FDA Drug Safety Communication: Safety review update of codeine use in children; new Boxed Warning and Contraindiction on use after tonsillectomy and/or adenoidectomy, downloaded from the Internet http://www.fda.gov/Drugs/DrugSafety/ucm339112.htm , (Sep. 23, 2016), 3 pages.

Fukuda, Tsuyoshi, et al., OCT1 genetic variants influence the pharmacokinetics of morphine in children, National Institutes of Health; *Pharmacogenomics*. Jul. 2013 ; 14(10): 1141-1151.

Goldman, Julie L., Mortality and Major Morbidity After Tonsillectomy: Etiologic Factors and Strategies for Prevention, The American Laryngological, Rhinological and Otological Society, Inc., vol. 123, (2013), pp. 2254-2553.

Höfle, Marion, et al., You can see pain in the eye: Pupillometry as an index of pain intensity under different luminance conditions, International Journal of Psychophysiology, vol. 70, (2008), pp. 171-175.

Horwood, Linda, et al., African American Ethnicity as a Risk Factor for Respiratory Complications Following Adenotonsillectomy, Jama Otolaryngol Head Neck Surg, vol. 139, No. 2, (Feb. 2013), pp. 147-152.

Kharasch, Evan D., et al., Intravenous and oral alfentanil as in vivo probes for hepatic and first-pass cytochrome P450 3A activity: Noninvasive assessment by use of pupillary miosis, American Society for Clinical Pharmacology and Therapeutics, vol. 86, No. 5, (Nov. 2004), pp. 452-466.

(56) References Cited

OTHER PUBLICATIONS

Kharasch, Evan et al., Role of hepatic and intestinal cytochrome P450 3A and 2B6 in the metabolism, disposition, and miotic effects of methadone, Clinical Pharmacology & Therapeutics, vol. 76, No. 3, (2004), pp. 250-269.
Lalovic, Bojan, et al., Quantitative Contribution of Cyp2d6 and Cyp3a to Oxycodone Metabolism in Human Liver and Intestinal Microsomes, The American Society for Pharmacology and Experimental Therapeutics, vol. 32, No. 4, (2004), pp. 447-454.
Larson, M.D., Pupillometry to Guide Postoperative Analgesia, Anesthesiology, vol. 116, No. 5, (May 2012), pp. 980-982.
Larson, Merlin D., et al., Pupillary Response to Noxious Stimulation During Isoflurane and Propofol Anesthesia, Anesth Analg, vol. 76, (1993), pp. 1072-1078.
Larson, Merlin D., Mechanism of opioid-induced pulillary effects, Clinical Neurophysiology, vol. 119, (2008), pp. 1358-1364.
Larson, Merlin D., The Effect of Antiemetics on Pupillary Reflex Dilation During Epidural/General Anesthesia, Anesth Analg, vol. 97, (2003), pp. 1652-1656.
Lee, H.K., et al., Mechanism of Morphine-Induced Miosis in the Dog, The Journal of Pharmacology and Experimental Therapeutics, vol. 192, No. 2, (1975), pp. 415-431.
Marcus, Carole, L., et al., A Randomized Trial of Adenotonsillectomy for Childhood Sleep Apnea, The New England Journal of Medicine, vol. 368, No. 25, (Jun. 20, 2013), pp. 2366-2376.
Marsch, Lisa A., et al., Effects of Infusion Rate of Intravenously Administered Morphine on Physiological, Psychomotor, and Self-Reported Measures in Humans, The Journal of Pharmacology and Experimental Therapeutics, vol. 299, No. 3, (2001), pp. 1056-1065.
Merkel, Sandra I., et al., The FLACC: A Behavioral Scale for Scoring Postopereative Pain in Young Children, Pediatr Nurs, vol. 23, No. 3, (May-Jun. 1997), pp. 293-297.
Murray, Rodney B., et al., The Pupillary Effects of Opioids, Life Sciences, vol. 33, No. 6, (1983), pp. 495-509.
Niesters, M., et al., Opioid-induced respiratory depression in paediatrics: a review of case reports, British Journal of Anaesthesia, vol. 110, No. 2, (2013), pp. 175-182.
Patino, M., et al., Obstructive sleep apnoea in children: perioperative considerations, British Journal of Anaesthesia, vol. 111, S1, (2013), pp. i85-i95.
Perquin, Christel W., et al., Pain in children and adolescents: a common experience, Pain, vol. 87, (2000), pp. 51-58.
Prows, Cynthia A., et al., Codeine-Related Adverse Drug Reactions in Children Following Tonsillectomy: A Prospective Study, Laryngoscope, vol. 124, (2014), pp. 1242-1250.
Rosen, Gerald M., et al., Postoperative Respiratory Compromise in Children With Obstructive Sleep Apnea Syndrome: Can It Be Anticipated?, Pediatrics, vol. 93, No. 5, (May 1994), pp. 784-788.
Sadhasivam, Senthilkumar, et al., Morphine clearance in children: Does race or genetics matter?, Journal of Opioid Management, vol. 8, No. 4, (Jul./Aug. 2012), pp. 217-226.
Sadhasivam, Senthilkumar, et al., Pharmacogenomics of opioids and perioperative pain management, Pharmacogenomics, vol. 13, No. 15, (2012), pp. 1719-1740.
Subramanyam, Rajeev, et al., Anesthesia- and opioids-related malpractice claims following tonsillectomy in USA: LexisNexis claims database 1984-2012, Pediatric Anesthesia, vol. 24, (2014), pp. 412-420.
Subramanyam, Rajeev, et al., Future of pediatric tonsillectomy and perioperative outcomes, International Journal of Pediatric Otorhinolaryngology, vol. 77, (2013), pp. 194-199.
Venkatasubramanian, Raja, et al., ABCC3 and OCT1 genotypes influence pharmacokinetics of morphine in children, Pharmacogenomics, vol. 15, No. 10, (Jul. 2014), pp. 1-24.
Voepel-Lewis, Terri, et al., Pain score guided morphine titration is risky and inappropriate, Pediatric Anesthesia, vol. 24, (2014), pp. 454-456.
Xia, Ying, et al., Ontogeny and distribution of opioid receptors in the rat brainstem, Brain Research, vol. 549, (1991), pp. 181-193.
Zhang, Zhenxiong, Activation of Opioid μ-Receptors in the Commissural Subdivision of the Nucleus Tractus Solitarius Abolishes the Ventilatory Response to Hypoxia in Anesthetized Rats, Anesthesiology, vol. 115, No. 2, (Aug. 2011), pp. 353-363.
Sadhasivam, S., et al. Race and unequal burden of perioperative pain and opioid related adverse effects in children, Pediatrics (2012); 129:832-8.
Miller, C.D., et al. Pupillary effects of alfentanil and morphine. British Journal of Anaesthesia (1990); vol. 65, pp. 415-417.
Segers, L. S., Functional connectivity in the pontomedullary respiratory network, Journal of Neurophysiology (2008), vol. 100, pp. 1749-1769.
Ding, Y.Q., et al., Immunohistochemical localization of mu-opioid receptors in the central nervous system of the rat, The Journal of Comparative Neurology (1996), vol. 367, pp. 375-402.

\* cited by examiner

QUANTITATIVE PUPILLOMETRY AS A BEDSIDE PREDICTOR OF POSTOPERATIVE RESPIRATORY DEPRESSION

CROSS-REFERENCE FOR RELATED APPLICATION

This application claims priority to U.S. Provisional Patent Application No. 62/117,171 filed on Feb. 17, 2015, the entire disclosure of which is hereby expressly incorporated by reference herein.

STATEMENT REGARDING FEDERALLY SPONSORED RESEARCH OR DEVELOPMENT

This invention was made with government support under RR026314 awarded by the National Institutes of Health. The government has certain rights in the invention.

BACKGROUND AND SUMMARY

The present invention relates generally to perioperative pain management and, more particularly to a non-invasive bedside tool for monitoring central nervous system effects of opioids, including postoperative respiratory depression.

Opioids are commonly used analgesics to manage severe pain following surgery in children. In the United States alone, approximately 6 million children undergo painful surgeries each year. However, inadequate pain relief and serious side effects from perioperative opioids occur in up to 50% of such children because clinicians continue to titrate morphine based on pain scores alone to gain satisfactory analgesia in children, despite the use of morphine for acute pain relief for over a century. Such a clinical practice fails to take into account increased central nervous system adverse effects caused with higher opioid doses. An example of a serious side effect caused by the use of opioids in children includes respiratory depression, which is a life-threatening adverse effect. These problems exist and continue to occur because of narrow therapeutic indices, large and unpredictable inter-patient variability in responses to opioids, and a lack of bedside biomarkers predictive of inter-individual pharmacodynamic variability and the morphine concentration-response relationship for acute pain management in children.

Thus, in order to optimize analgesia while avoiding unnecessary adverse effects, better and/or proactive risk prediction and tailored interventions are desired. With current standard clinical practice, it is difficult to proactively identify children at risk for serious opioid adverse effects at bedside. Safe and effective analgesia following surgery is an unmet clinical need in children as a result of our incomplete understanding of central nervous system (CNS) effects of opioids in terms of pharmacokinetics and predictive tools of opioid-induced respiratory depression.

A quantitative pupillometry (QP) system of the present disclosure may serve as a real-time tool to guide opioid titration, and has substantial potential for optimizing analgesia and reducing central nervous system adverse effects by opioids, including respiratory depression. This quantitative pupillometry system may identify children at risk for central opioid adverse effects, especially respiratory depression, before they occur clinically based on high sensitivity and reliability of serial quantitative pupillometry measures in children. Thus, the use of the quantitative pupillometry system of the present disclosure may avoid prolonged hospital stays and deaths associated with opioid-induced respiratory depression.

The illustrative quantitative pupillometry system of the present disclosure is a non-invasive innovative bedside tool for monitoring CNS effects of opioids. Opioids such as morphine cause miosis and altered pupillary reaction time. Bedside quantitative pupillometry is shown to be safe, non-invasive, well-tolerated by children of 1 to 18 years of age, and relatively easy to use with minimal training. The pupillary response to painful stimuli has been proven to be a more sensitive marker than the associated hemodynamic changes of heart rate and systolic blood pressure in children under sevoflurane anesthesia with pupillometry values showing a significant increase in pupil size immediately after the skin incision followed by a rapid decrease in pupil size immediately after the administration of alfentanil. Though quantitative pupillometry has been successfully used to measure CNS analgesic effects of opioids, it has not been studied to assess opioid's risk of CNS adverse effects such as respiratory depression in children.

Illustratively, the quantitative pupillometry system of the present disclosure includes a handheld pupillometer for use as a bedside, real-time, non-invasive tool to proactively predict an individual child's risk for postoperative respiratory depression. Preliminary perioperative morphine pharmacokinetic data, serial quantitative pupillometry, clinical outcome and genetic data from 300 children undergoing tonsillectomy suggest that inter-individual variability in response to morphine in children can be predicted and better assessed at bedside by quantitative pupillometry. Some children are at higher risk than others for respiratory depression and it is hard for clinicians to proactively identify at-risk children and tailor their use of opioids. Preoperative genotyping and monitoring of safe opioid levels are not routinely performed in children undergoing surgical procedures to identify and minimize an individual's risk with opioids. Current practice of morphine administration is based on pain scores alone and is suboptimal and risky as it does not balance against increased adverse effects including respiratory depression with higher opioid doses. Preliminary data suggest that serial quantitative pupillometry measures correlate with morphine's pharmacokinetics and can potentially help to identify children at risk of postoperative respiratory depression.

The illustrative quantitative pupillometry system is configured to tailor perioperative pain management in children to individual needs, to improve safety and reduce cost of perioperative care with the right dose of the right analgesic for each child. The illustrative system is configured to determine how serial non-invasive objective quantitative pupillometry measures correlate with morphine's pharmacokinetics and postoperative respiratory depression in children. The system is based on perioperative quantitative pupillometry measures in children correlating with morphine's pharmacokinetics and proactively predicting postoperative opioid-related respiratory depression.

The illustrative quantitative pupillometry system as a non-invasive, real-time, sensitive bedside tool to objectively measure pupil size and its reaction to light, can be an effective method of assessing CNS effects of opioids. Once morphine's pharmacokinetics and CNS pharmacodynamics are reliably and non-invasively captured with the quantitative pupillometry, it will be possible to better identify children at risk for postoperative opioid-induced respiratory depression without invasive serial pharmacokinetic sampling when lacking routine preoperative genotyping.

Operation of the quantitative pupillometry system is based on the following principles: (1) determining pupillary effects of intraoperative morphine and correlating with morphine's pharmacokinetics in children undergoing tonsillectomy; and (2) predicting postoperative opioid-induced respiratory depression in children undergoing tonsillectomy with perioperative quantitative pupillary measures.

The quantitative pupillometry system of the present disclosure is an innovative bedside biomarker of CNS effects and pharmacokinetics of opioids that narrows the current critical knowledge gap by proactively identifying children at risk for postoperative respiratory depression. This enables proactive risk prediction and thereby personalized use of the right analgesics at the right dose in children to maximize pain relief while minimizing adverse effects.

According to an illustrative embodiment of the present disclosure, a quantitative pupillometry system for predicting postoperative respiratory depression includes a pupillometer having an image acquisition device and a stimulus light source, the image acquisition device being configured to detect pupillary effects from a pupil of a patient in response to light from the stimulus light source being applied to the pupil. The quantitative pupillometry system further includes a memory unit storing opioid pharmacokinetic data, and a processor in communication with the pupillometer and the memory unit. The processor includes a pharmacokinetic association module for associating the opioid pharmacokinetic data with anticipated pupillary effects, and a respiratory depression prediction module for predicting a probability of opioid-related respiratory depression by comparing the anticipated pupillary effects from the pharmacokinetic association module and the detected pupillary effects from the pupillometer. The quantitative pupillometry system further includes a user interface in communication with the processor, the user interface being configured to provide the prediction of the probability of opioid-related respiratory depression from the respiratory depression prediction module to a user.

According to a further illustrative embodiment of the present disclosure, a quantitative pupillometry system for predicting a probability of at least one opioid-related central effect includes a pupillometer including an image acquisition device and a stimulus light source, the image acquisition device being configured to detect pupillary effects from a pupil of a patient in response to light from the stimulus light source being applied to the pupil. The quantitative pupillometry system further includes a processor in communication with the pupillometer, the processor including an opioid-related central effect prediction module for predicting a probability of at least one opioid-related central effect in response to the pupillary effects detected by the pupillometer. The quantitative pupillometry system further includes a user interface in communication with the processor, the user interface being configured to display the prediction of the probability of the at least one opioid-related central effect from the processor to a user.

According to another illustrative embodiment of the present disclosure, a method of predicting a probability of at least one opioid-related central effect includes the steps of administering an opioid to a patient, stimulating a pupil of the patient, and acquiring an image of the stimulated pupil. The method further includes the steps of detecting pupillary effects of the pupil, predicting a probability of at least one opioid-related central effect based upon the detected pupillary effects, and providing the predicted probability of the at least one opioid-related central effect to a user.

In various aspects of the above embodiments, the memory unit is configured to receive and process the opioid pharmacokinetic data. Furthermore, in various aspects, the at least one opioid-related central effect includes respiratory depression, sedation and/or vomiting.

Additional features and advantages of the present invention will become apparent to those skilled in the art upon consideration of the following detailed description of the illustrative embodiments exemplifying the best mode of carrying out the invention as presently perceived.

BRIEF DESCRIPTION OF THE DRAWINGS

The detailed description of the drawings particularly refers to the accompanying figures in which.

DETAILED DESCRIPTION OF THE DRAWINGS

Figure 1:
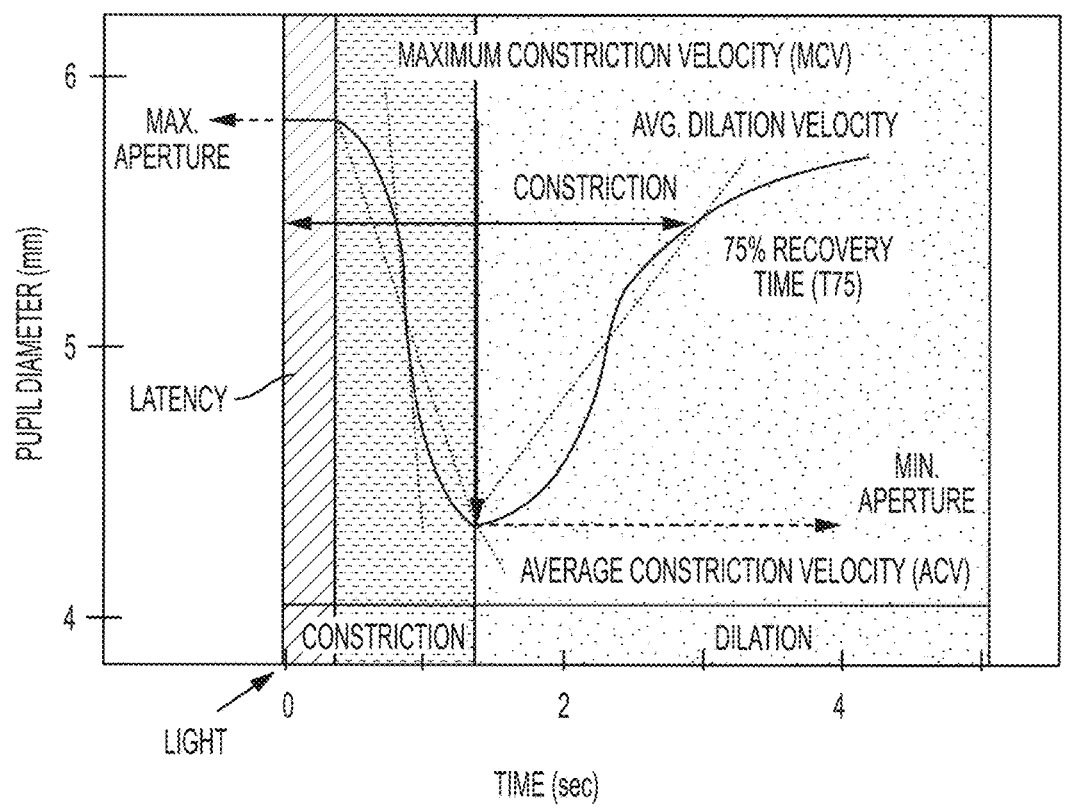
FIG. 1 is an illustrative graph showing pupil response to light from a pupillometer.
Figure 2A:
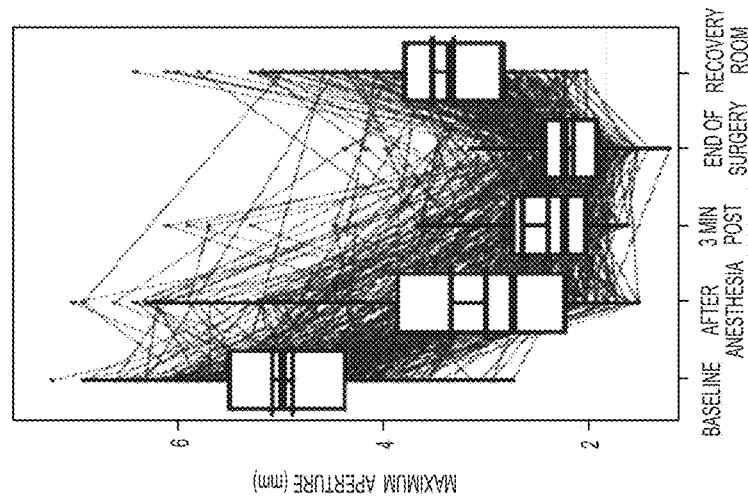
FIG. 2A is a chart showing pupil maximum aperture in relation to intraoperative morphine bolus.
Figure 2B:
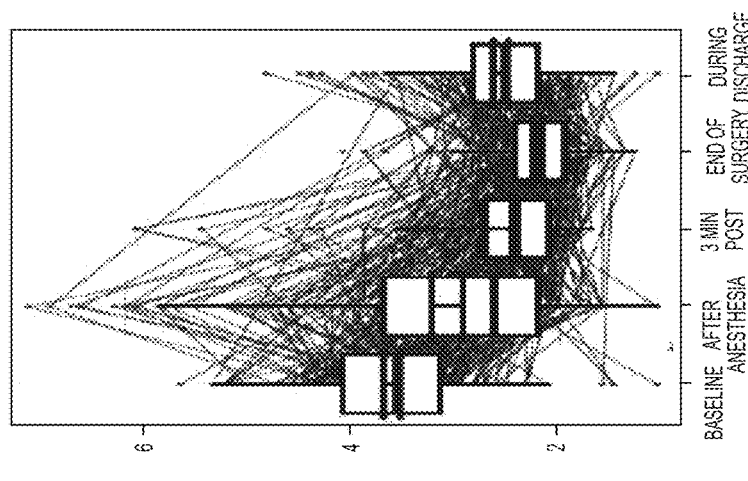
FIG. 2B a chart showing pupil minimum aperture in relation to intraoperative morphine bolus.
Figure 2D:
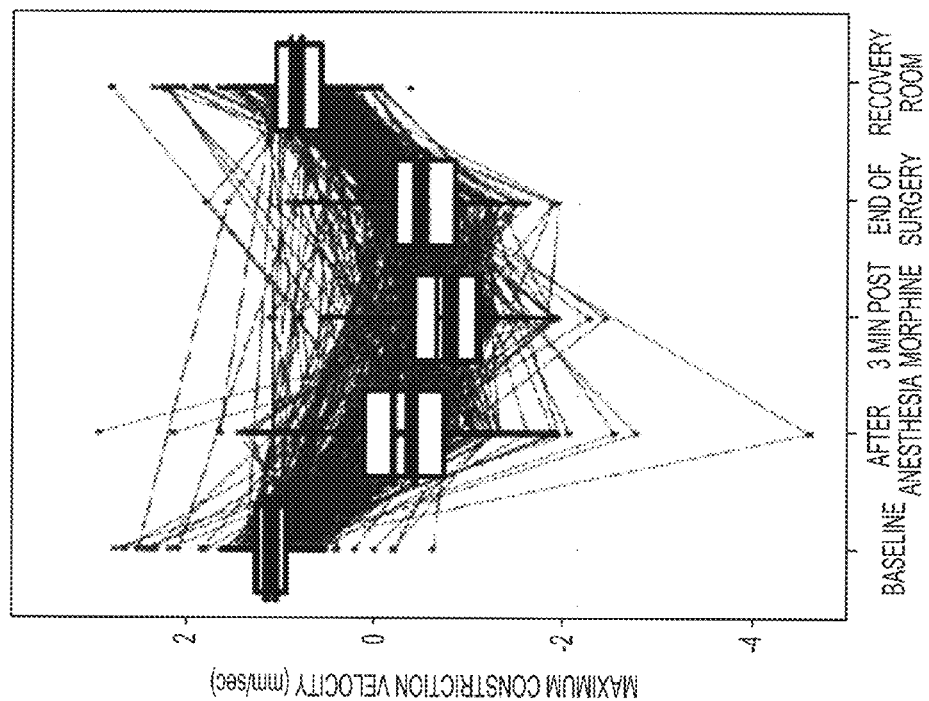
FIG. 2D a chart showing pupil maximum constriction velocity in relation to intraoperative morphine bolus.
Figure 2C:
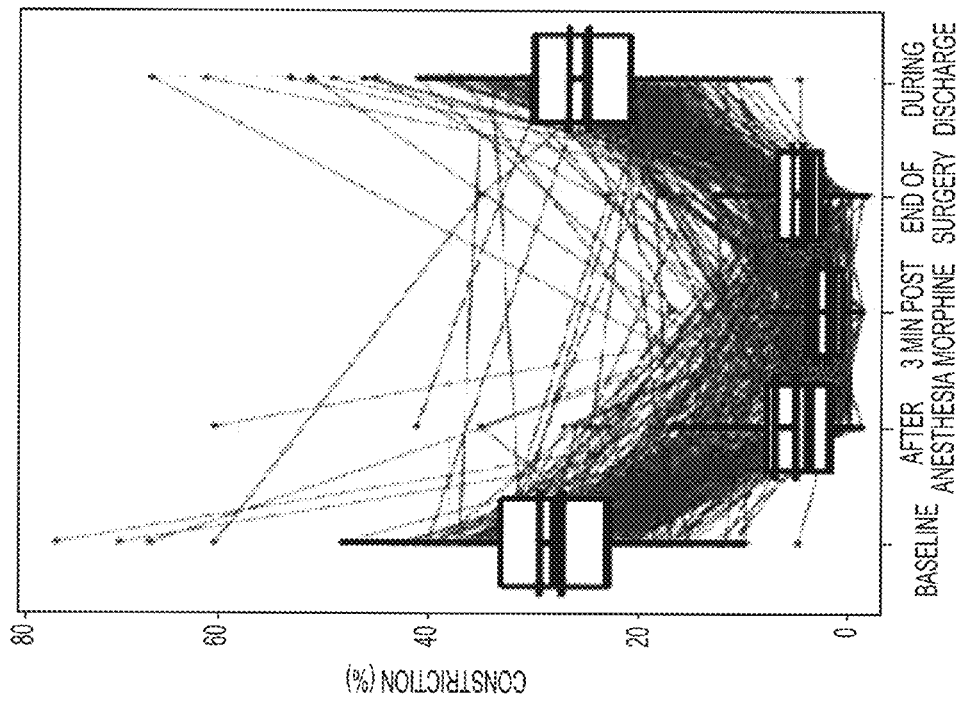
FIG. 2C a chart showing pupil constriction percentage in relation to intraoperative morphine bolus.

The embodiments of the invention described herein are not intended to be exhaustive or to limit the invention to precise forms disclosed. Rather, the embodiments elected for description have been chosen to enable one skilled in the art to practice the invention.

Quantitative pupillometry can be easily used at bedside by clinical care providers with minimal training. As further detailed herein, certain quantitative pupillometry measures proactively predict respiratory depression before it happens. This can be used as a sensitive central nervous system monitoring tool before caregivers give additional opioid pain medications and central depressants, such as benzodiazepines, to avoid respiratory depression. Quantitative pupillometry measures can also be used to complement genotype-based (genetic variants of ABCB1, FAAH, OPRM1 genes) personalized interventions to minimize respiratory depression risk while improving pain relief. Quantitative pupillometry measures can be used to stratify patients' respiratory depression risk as "high risk", "medium risk" and "low risk" in addition to monitoring recovery from or progress towards respiratory depression as a trend monitor. Once simplified and validated, certain quantitative pupillometry measures can be integrated as a real-time feedback loop system to improve safety of opioid infusion using smart infusion pumps including Patient Controlled Analgesia (PCA) smart pumps.

In adult pharmacokinetic (PK) studies, pupillometric measures have been compared with plasma PK values obtained at the same time points and were shown to provide a reasonable reflection of the alfentanil plasma concentration-time profile. Pupillary diameter changes have been utilized as a marker of opioids' pharmacodynamic response in many adult studies. Quantitative pupillometry responses are more sensitive than hemodynamic responses to noxious stimuli and they are also early indicators of neurological outcomes following cardiac resuscitation, highlighting quantitative pupillometry's high sensitivity as an early indicator. Pupillary response to pain and analgesia is a reliable tool for objectively quantifying the level of pain in situations where a subjective pain score cannot be obtained.

Highly sensitive digital handheld pupillometers have made the measurement of pupillary size and response to light, pain and opioid analgesia feasible in children. Quantitative normative data has been generated using hand-held pupillometer in healthy 1-18 year old pediatric volunteers. Handheld pupillometers are considered safe, non-invasive, well-tolerated by children, and relatively easy to use with minimal training. The pupillary response to painful stimuli has been proven to be a more sensitive marker than the associated hemodynamic changes of heart rate and systolic blood pressure in children under sevoflurane anesthesia with pupillometry values showing a significant increase in pupil size immediately after the skin incision followed by a rapid decrease in pupil size immediately after the administration of alfentanil. Capturing the extent of pupil dilation can provide an index of acute nociceptive input via autonomic innervation of the iris muscles, while capturing the extent of attenuation in this pupillary response during exposure to opioids can provide insight into opioids' CNS effect by reflecting the extent of occupancy of opioid receptors in the CNS.

In an illustrative clinical pediatric study, children 6-15 years old of both sexes and all races were recruited. Children with American Society of Anesthesiologists (ASA) physical status 1 or 2 scheduled for tonsillectomy for recurrent tonsillitis, adenotonsillar hypertrophy or obstructive sleep apnea (OSA) were included. Clinical criteria for OSA included sleep disordered breathing with a history of snoring and either sleep pauses lasting >10 seconds or daytime drowsiness. Exclusion criteria include non-English speaking families, children with morphine allergy, developmental delay, liver and renal diseases, and preoperative pain requiring analgesics (e.g. chronic tonsillitis). Children who have problems with pupil or pupillary reaction due to disease (e.g. amyloidosis, Homer's syndrome, familial dysautonomia, other eye and neurological disorders) or on medications influencing pupillary size (anti-cholinergic, narcotic medications such as codeine in cough syrup) were not recruited.

All pediatric study participants received standard perioperative care. Anesthesia was induced using sevoflurane followed by a propofol (2 mg/kg) bolus to facilitate endotracheal intubation. Anesthesia was maintained with sevoflurane without the use of neuromuscular blockade. Children received a standard dose of intravenous morphine prior to surgical incision. Children with OSA history received 0.1 mg/kg morphine while those without OSA diagnosis received 0.2 mg/kg. Tonsillectomy was done using electrocautery surgical technique. If there were any signs suggestive of pain (clinically significant increase in heart rate and blood pressure) following surgical incision, the clinical team provided additional morphine at 0.05 mg/kg increments. All children received prophylactic ondansetron (0.1 mg/kg) and dexamethasone (0.1 mg/kg) intraoperatively. Significant postoperative pain measured with facial expression; leg movement; activity; cry; and consolability (FLACC) pain score of ≥4/10 was managed in the postoperative anesthesia care unit (PACU) with rescue doses (0.05 mg/kg) of morphine.

The pediatric study included the following data collection: 1) pharmacokinetic (PK)—serial blood samples to determine concentrations of morphine and its metabolites; 2) pharmacodynamic (PD)—utilization of serial QP measures (serial QP pupillometry in this study was done strictly for research purposes), validated pain scoring systems and incidences of postoperative respiratory depression; and 3) pharmacogenetic (PG)—genotype children with regard to ABCB1 transporter, UGT2B7, and other pain and opioid pathway relevant genotypes.

The pediatric study also included pharmacokinetic sampling and analysis. More particularly, serial blood samples were obtained from children to quantify blood Morphine, Morphine-3 Glucuronide (M3G) and Morphine-6 Glucuronide (M6G) concentrations (see table below). For ethical reasons, blood samples were not obtained if the child was fully recovered from anesthesia and uncooperative in the recovery room. Morphine, M3G and M6G were quantified using a validated highly sensitive liquid chromatography tandem mass spectrometry assay. The limits of quantification were 0.25-1000 ng/ml ($r2>0.99$) for morphine and 1-1000 ng/ml ($r2>0.99$) for both M3G and M6G.

|    | Before Surgery Baseline | During Surgery Under Anesthesia in Operating Room (OR) | After Surgery Recovery Room- PACU |
|---|---|---|---|
| PK |  | Blood draw for morphine and metabolites, M3G and M6G levels, immediately following IV insertion (pre-morphine baseline), 3 minutes and 15 minutes after morphine bolus | Blood draw for morphine, M3G and M6G levels 30-45 minutes after morphine bolus |
| D | Quantitative Pupillometry (QP) at baseline HR, BP, RR Baseline Pain Scores | QP at beginning of anesthesia; 3 minutes after initial morphine bolus (before surgical incision) and at the end of surgery (typically 20 minutes from initial morphine bolus) & - HR, BP, RR | QP in recovery room HR, BP, RR & Pain Scores Respiratory depression |
| PG |  | Blood sample collection to evaluate ABCB1 & other important and exploratory genetic variants |  |

The pediatric study included quantitative pupillometry (QP) measurements and analysis of pupillary responses to opioids. More particularly, in the pediatric study, a pupillometer 102 was used to measure pupil diameter and response dynamics using standardized procedure and perioperative lighting. A soft rubber cup 112 on the pupillometer 102 was first placed around the child's eye 114. The resting (maximum) pupil diameter, maximum and average pupil constriction velocities (mm/s), minimum diameter, constriction amplitude (maximum minus minimum diameter), and relaxation velocity (mm/s) were all recorded. As shown in FIG. 1, each of the measurements can be determined from a chart recording pupil diameter in millimeters at a given time in seconds. The procedure is brief (<5 sec), non-invasive and has no associated risk. Because of strong association between postoperative pain scores and pupillary dilation reflex, pupillometer could be a valuable tool to guide morphine administration for pain relief in the immediate postoperative period in controlled situations when confounding factors are well controlled such as in the subject pediatric study.

The pediatric study used a standardized sevoflurane and propofol (to facilitate endotracheal intubation) anesthesia without neuromuscular blocking and reversal agents (e.g. atropine), and antiemetics that could affect pupillary responses (droperidol, metoclopramide). The pediatric study used ondansetron as a prophylactic antiemetic which does not interfere with quantitative pupillometry responses.

In the pediatric study population, as shown in the FIGS. 2A-2D, pupillary sizes and reaction pattern followed a consistent pattern perioperatively. Compared to baseline preoperative values, under general anesthesia, maximum and minimum pupillary sizes and constriction percentage and maximum constriction velocity decreased. After intraoperative morphine there were incremental reductions in all these pupillary measures and pupillary recovery was observed towards the end of anesthesia and further recovery in PACU. Compared to the baseline values, PACU measures showed residual depressive effects of morphine.

The pediatric study confirms an association between blood morphine concentration and postoperative respiratory depression. Surprisingly, children who had respiratory depression and had prolonged PACU stay due to respiratory depression had lower morphine (2.25±2.3 vs. 8.4±7.9 ng/ml, p<0.0001), lower M6G (9.1±3.9 vs.11.7±7.1 pg/ml) and lower M3G (43.1±37 vs.60.7±45.1 pg/ml) levels in the recovery room than those who did not possibly suggesting a role of CNS pharmacodynamic variability to morphine-induced respiratory depression despite lower morphine and metabolite concentrations. This could be potentially explained by higher sensitivity of certain children based on genetic variants of ABCB1 and other genes affecting central morphine concentrations compared to blood morphine and metabolite concentrations. Perioperative pupillometry measures (e.g. Maximum Constriction Velocity) correlated well with perioperative morphine plasma concentrations in the pediatric study.

Figure 3:
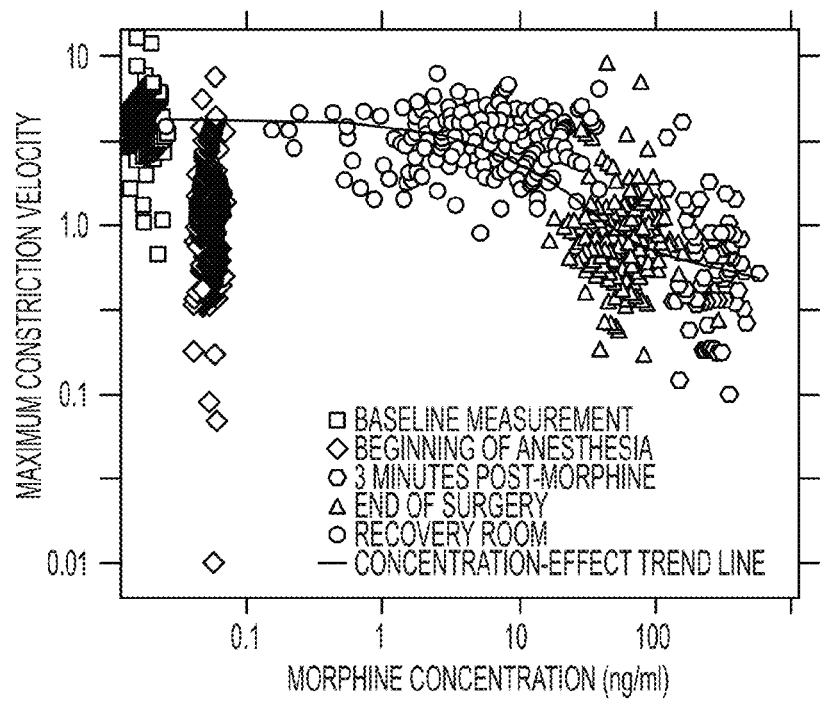
FIG. 3 is an illustrative graph showing pupil maximum constriction velocity in relation to morphine concentration.

FIG. 3 shows the association between blood morphine concentration and pupil Maximum Constriction Velocity (MCV). More particularly, pupillary maximum constriction velocity (MCV) decreased as blood morphine concentration increased. The highest morphine concentration and lowest MCV were observed immediately after morphine administration, followed by at the end of surgery and in the recovery room, highlighting that this pupillary measure is a non-invasive measure of morphine's central pharmacokinetics and central pharmacodynamic pupillary effect. The effect of anesthesia on MCV was negligible and was similar to baseline MCV values with no detectable morphine levels.

PK-PD (and PG) modeling was also used in the pediatric study. The population PK model that captures morphine and metabolite concentration profiles was used to correlate with simultaneous quantitative pupillometry measures. The relationship between morphine exposure and quantitative pupillometry measures was then evaluated using NONMEM to estimate population mean, inter-individual variability and intra-individual model parameters. NONMEM is a known software package used for population pharmacokinetic modeling, and is available from ICON plc of Dublin, Ireland.

Non-linear mixed effects modeling was constructed to link the blood morphine and metabolite levels to PD effects including serial quantitative pupillometry measures and postoperative respiratory depression, and with important genetic predictors in sophisticated PK-PD-PG models. Variations in brain concentrations of morphine and metabolites could result from 1) blood brain barrier transport variations (e.g. ABCB1 polymorphisms), and 2) variations in plasma concentrations, which could be determined by development-related clearance differences (e.g. age), and variations in morphine metabolisms (e.g. UGT2B7 and other important polymorphisms). Important genetic variants in morphine's metabolic pathway were genotyped using PCR (TaqMan) and Human Illumina Omni5 GWAS platforms in 300 children in the pediatric study.

During analysis, descriptive data of all quantitative pupillometry measures (mean, standard deviation) were analyzed. The differences between children with and without postoperative respiratory depression on these quantitative pupillometry measures using either t-tests or Wilcoxon rank-sum test depending on the distribution were analyzed. Three-way associations between serial QP measures, serial blood morphine concentrations and postoperative respiratory depression were performed. Sophisticated morphine PK-PD modeling for quantitative pupillometry measures and respiratory depression would be developed in a larger sample in our ongoing study and quantitative pupillometry measures will also be correlated with postoperative Hypercapneic Ventilatory Response (HVR), which is an objective and early indicator of impending clinical respiratory depression.

The pediatric study confirmed the feasibility of quantitative pupillometry as a bedside tool to assess postoperative respiratory depression in children. The preliminary data demonstrates encouraging associations between postoperative respiratory depression with 1) pupillary constriction difference at the end of surgery and baseline measure (p=0.009), and 2) time to 75% pupillary recovery (T75) difference between measures from PACU and baseline (p=0.036). In addition, we found significant associations between postoperative respiratory depression resulting in prolonged PACU stay and 1) pupillary average constriction velocity (ACV) differences obtained 3 minutes after morphine and baseline (p=0.018), 2) maximum constriction velocity (MCV) differences obtained 3 minutes after morphine and baseline (p=0.006) and 3) MCV difference obtained in the PACU and at baseline (p=0.02), in addition time to 4) 75% pupillary size recovery differences between measures obtained in the PACU and baseline (p=0.04). Before children arrive in PACU, these potentially predictive early quantitative pupillometry measures would help stratify their respiratory depression risk upon arrival to PACU and choose targeted interventions with non-opioid analgesics if needed.

In the pediatric study, clinical respiratory depression was defined as a persistent (>1 minute) oxygen desaturation (SpO2) <90% or respiratory rate <8 breaths per minute or SpO2<94% along with respiratory rate <10 per minute requiring supplemental oxygen to maintain SpO2>94% in the absence of upper airway obstruction. If a child required >90 minutes to meet PACU discharge criteria following tonsillectomy, it was defined as a prolonged PACU stay. Analgesic outcome measures are maximum postoperative pain scores, intravenous analgesic interventions in PACU (yes/no) and post-operative morphine doses (mg/kg). The maximum postoperative pain score for each child was generated from postoperative pain scores assessed in PACU at multiple time points using a 0 to 10 FLACC pain scale.

Figure 4:
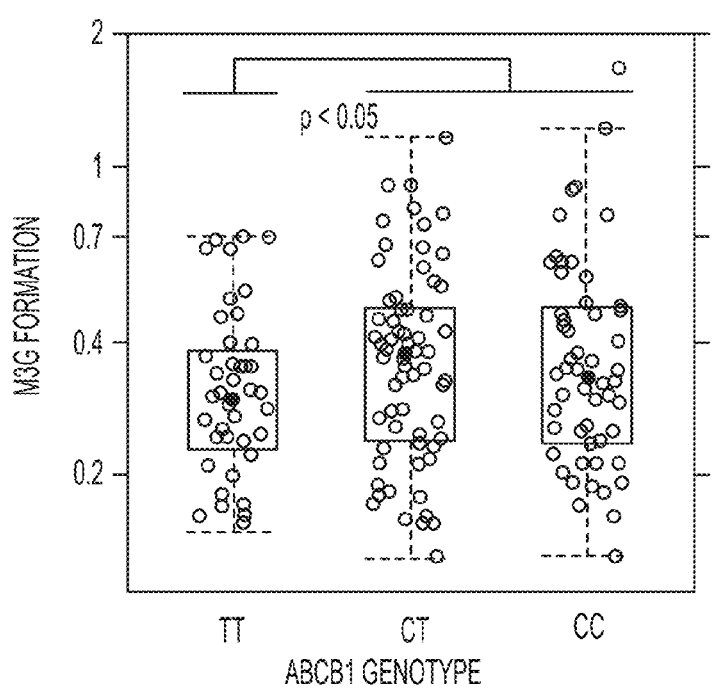
FIG. 4 is an graph showing morphine metabolite formation compared to ABCB1 genotypes.

With reference to FIG. 4, postoperative respiratory depression and its association with ABCB1 genetic variants are demonstrated. Morphine is subject to efflux via P-glycoprotein transporter encoded by ABCB1, also known as MDR1. ABCB1 polymorphisms may affect blood brain barrier transport of morphine and therefore individual response to its CNS effects. Preliminary data in 263 children undergoing tonsillectomy showed that children with GG and GA genotypes of ABCB1 polymorphism rs9282564 had higher risks of respiratory depression resulting in prolonged hospital stays. Thus, adding one copy of the minor allele (G) increased the odds of a prolonged hospital stay due to postoperative respiratory depression by 4.7 fold (95% CI: 2.1-10.8, p=0.0002).

With further reference to FIG. 4, ABCB1 genetic variants and morphine metabolite formation clearance is shown. In pediatric morphine pharmacokinetic-pharmacogenetic modeling, it has been discovered that children with CT and CC genotypes of ABCB1 SNP, C3435T (rs1045642) had 18.4% higher metabolite formation clearance, FCLM3G, than subjects with TT genotype (p=0.04).

The above preliminary data on ABCB1's role on morphine's pharmacokinetics (liver transport) and respiratory depression (blood-brain barrier transport) are important as they can guide optimal analgesic concentrations and assess potential respiratory depression risk at bedside.

With reference to FIGS. 5-8, the illustrative quantitative pupillometry (QP) system 100 of the present disclosure is a non-invasive innovative marker for monitoring the CNS concentration-effect-time relationship of opioid analgesics and as a result can serve as a biomarker for individual opioid's CNS effects such as analgesia and potentially for respiratory depression. The illustrative quantitative pupillometry (QP) system 100 includes a pupillometer 102 having an image processing module 104, illustratively defined by a small computer with a color LCD screen supported by a hand-held housing 106. The housing 106 further supports an integral illumination or light source 108 and a self-contained image acquisition device 110, illustratively a charge-coupled camera or digital camera. A soft rubber eye cup 112 aligns the light source 108 with the patient's eye 114 for directing light 116 to the patient's pupil 118. The light source 108 is illustratively an infrared (IR) light source that illuminates the eye 114 with a set of infrared light rays 116 at 850 nm. The image acquisition device 110 measures size and dynamics of the pupil 118, as represented by image acquisition line 120. Images are acquired by the image acquisition device 110 in 5 to 10 seconds/eye and analyzed by the image processing module 104 within 3-4 seconds.

Additional details of pupillometers that may be used with the system 100 of the present disclosure are provided, for example, in U.S. Pat. No. 4,755,043 to Carter, U.S. Pat. No. 4,850,691 to Gardner et al., U.S. Pat. No. 6,199,985 to Anderson, and U.S. Pat. No. 8,235,526 to Stark et al., the disclosures of which are expressly incorporated by reference herein. In one illustrative embodiment, the pupillometer may be the NeurOptics™ PLR-100 infrared pupillometer, available from Neuroptics, Inc. of San Clemente, Calif.

Figure 6:
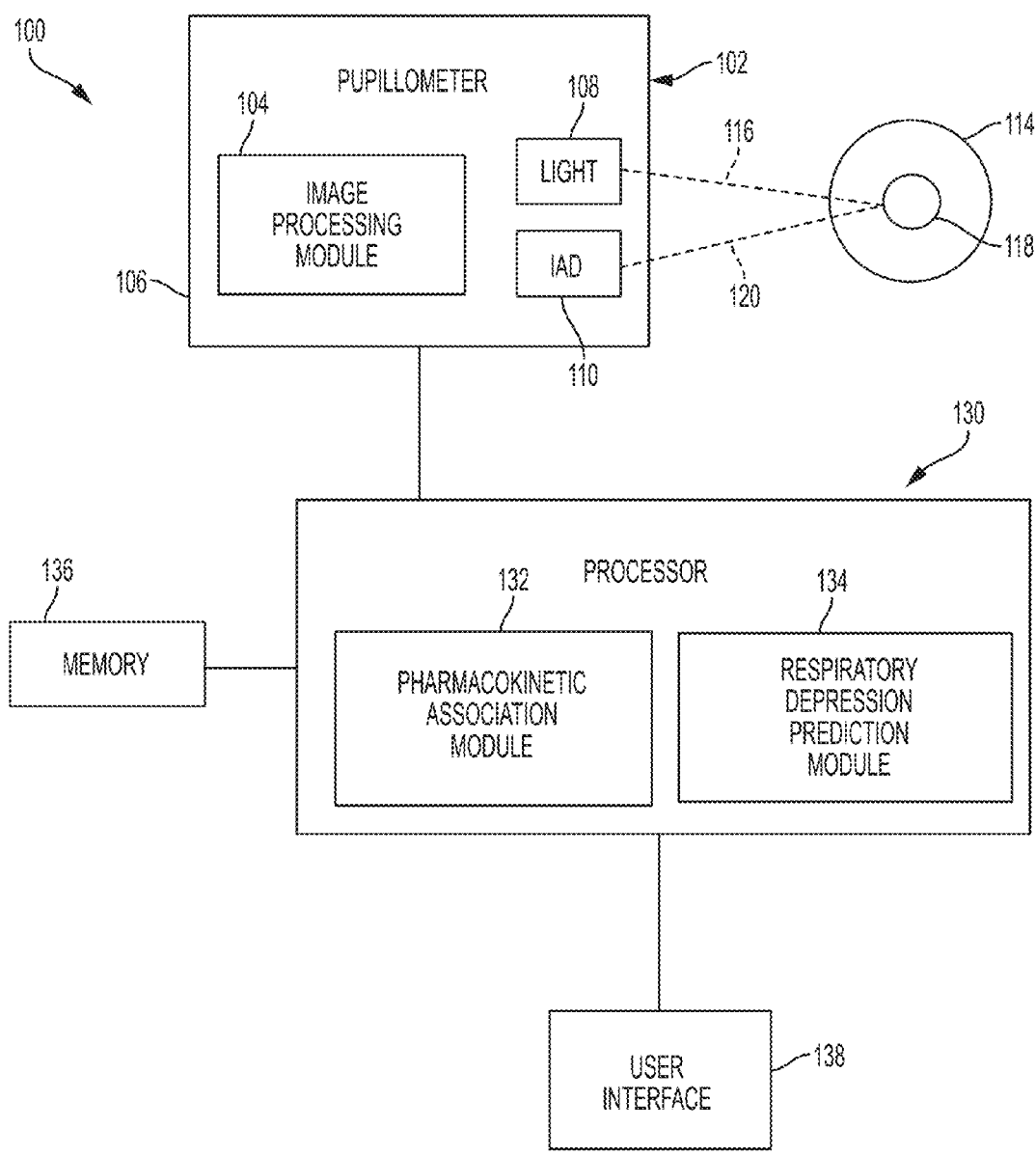
FIG. 6 is a block diagram of an illustrative quantitative pupillometry system of the present disclosure.

In further detail and referring to FIG. 6, a processor 130 is in electrical communication with the image processing module 104 of the pupillometer 102. Processor 130 generally includes a respiratory depression prediction module 134. In various embodiments, processor 130 may further include a pharmacokinetic association module 132, wherein the pharmacokinetic association module 132 may be in communication with a memory unit 136. In the illustrative embodiment of FIG. 6, the processor 130 includes both the pharmacokinetic association module 132 and the respiratory depression prediction module 134. Additionally, the memory unit 136 is in electrical communication with the processor 130. The memory unit 136 illustratively stores pharmacokinetic data on administered opioids, and supplies this data to the pharmacokinetic association module 132. In various illustrative embodiments, memory unit 136 may also receive and/or process the opioid pharmacokinetic data. In an exemplary embodiment, memory unit 136 may receive and/or process the data in real-time (e.g., less than one minute after surgery). For example, the data may include morphine and metabolite levels measured at bedside.

The pharmacokinetic association module 132 is configured to associate opioid pharmacokinetics stored within the memory unit 136 with anticipated pupillary effects from the image processing module 104 of the pupillometer 102. The respiratory depression prediction module 134 is configured to predict a probability of postoperative opioid-related respiratory depression by comparing the anticipated pupillary effects from the pharmacokinetic association module 132 with the detected pupillary effects from the pupillometer 102. In various embodiments, the respiratory depression prediction module 134 may be configured to predict the probability of postoperative opioid-related respiratory depression by analyzing the detected pupillary effects from the pupillometer 102 and/or comparing such detected pupillary effects with historical data associating various pupillary effects with postoperative opioid-related respiratory depression. Such historical data may be stored within the memory unit 136 and include, for example, a difference of pupillary constriction over time, a difference of pupillary average constriction velocity over time, a difference of maximum constriction velocity over time, and a difference of pupillary size recovery over time.

Furthermore, a user interface 138 is illustratively in electrical communication with the processor 130 and is configured to provide the prediction of respiratory depression from the respiratory depression prediction module 134 to a user. The user interface 138 may comprise a computer monitor or display screen to provide a visual indication to the user.

Figure 5:
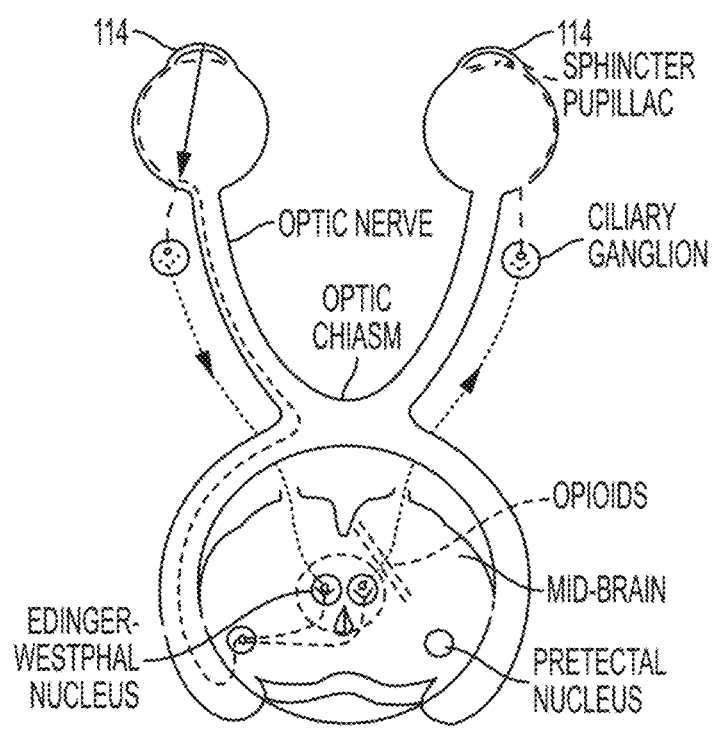
FIG. 5 is a diagrammatic representation of pathways and nerve centers that control pupil size and pupillary light reflex in humans.

With further reference to FIG. 5, the illustrative quantitative pupillometry (QP) system 100 uses QP measures as biomarkers of opioid-induced respiratory depression. More particularly, this sensitive and early indicator of CNS opioid effects is used to associate with morphine pharmacokinetics and opioid's CNS adverse effect, or respiratory depression in children. Opioids such as morphine cause miosis and altered pupillary reaction time. Miosis, or constriction of the pupil, is caused by normal light reflex and also occurs in response to specific μ-opioid receptor agonists. Opioid-induced miosis is mediated by the parasympathetic nervous system. Opioid-induced miosis and other pupillary effects can be observed immediately after opioid administration highlighting its sensitivity and early response.

Figure 7:
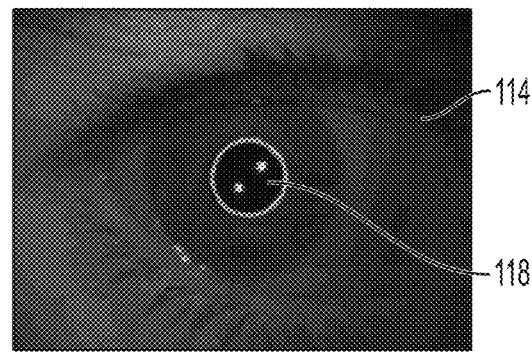
FIG. 7 is a front perspective view of a patient's eye including pupil.
Figure 8:
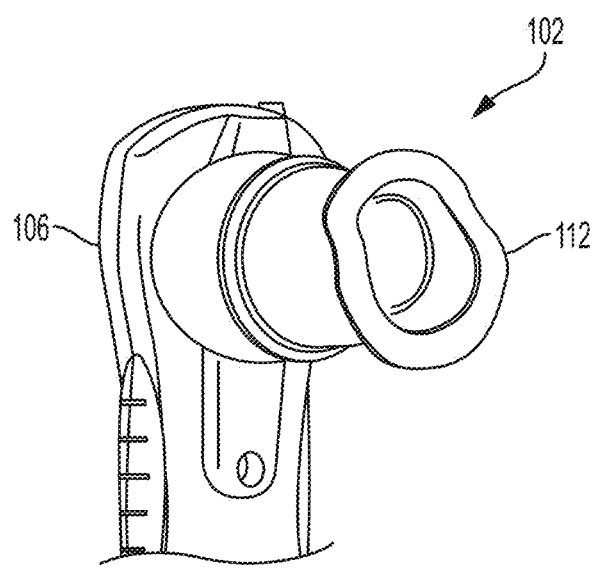
FIG. 8 is a front perspective view of an illustrative pupilometer.

With further reference to FIGS. 5-7, the brief retinal light 108 of the pupillometer 102 induces miosis with pupillary light reflex. The pupillary light reflex starts with the photosensitive ganglion cells in the retina which transmit information to the optic nerve which in turn is connected to the superior colliculus of the midbrain, and neurons of the Edinger-Westphal nucleus, whose motor neurons run along bilateral oculomotor nerves which innervate the constrictor muscle of the iris, thus producing miosis. The mechanism of opioids on pupil response is that pupillary constrictor neurons of the oculomotor nuclear complex increase frequency of discharge in response to µ-opioid agonists. It is important to note that the Edinger-Westphal nucleus in midbrain is in close proximity to medullary respiratory centers in humans, where µ-opioid receptors are densely populated and functionally connected. Opioids such as morphine exert their CNS effects including analgesia, respiratory depression and miosis with µ-opioid agonism, making quantitative pupillometry a potential sensitive and early bedside non-invasive tool to assess morphine's CNS analgesia and adverse effects in children undergoing surgery.

In an illustrative method of operation, the quantitative pupillometry system 100 may be used to predict the probability of postoperative respiratory depression in response to the administration of an opioid to a patient. The method illustratively includes the steps of administering an opioid, such as morphine, to the patient, and stimulating the pupil 118 of the patient via activation of the light source 108 of the pupillometer 102. The method further includes the steps of acquiring an image of the stimulated pupil 118 through the image acquisition device 110 of the pupillometer 102. Next, the image processing module 104 of the pupillometer 102 detects pupillary effects of the pupil 118.

The method continues with the processor 130 predicting a probability of postoperative opioid-related respiratory depression based upon the detected pupillary effects from the image processing module 104. The prediction is based upon at least one of a difference of pupillary constriction over time, a difference of pupillary average constriction velocity over time, a difference of maximum constriction velocity over time, and a difference of pupillary size recovery over time.

The predicted probability of postoperative opioid-related respiratory depression is then provided to a user interface 138. The user interface 138 may be configured for use by caregivers at bedside. Illustratively, the user interface 138 may include conventional input devices, such as a keyboard or tablet, and/or conventional output devices, such as a computer display or printer. In other illustrative embodiments, the user interface 138 may be in communication with a pain management system, such as an analgesia pump.

Respiratory depression has been used as an illustrative embodiment throughout the present description. It should be understood that other opioid-related central effects (i.e., central nervous system effects) may be used in place and/or in addition to respiratory depression. In various illustrative embodiments, other opioid-related central effects may include sedation and/or vomiting. Additionally, while the specification has generally referred to the various steps or actions being carried out postoperative, any and/or all of the various steps or actions may occur at any other time. For example, the various steps or actions may be carried out preoperative or they may occur in non-surgical settings.

Although the invention has been described in detailed with reference to preferred embodiments, variations and modifications exist within the spirit and scope of the invention as described and defined in the following claims.

The invention claimed is:

1. A quantitative pupillometry system for predicting respiratory depression comprising:
   a pupillometer including an image acquisition device and a stimulus light source, the image acquisition device configured to detect pupillary effects from a pupil of a patient in response to light from the stimulus light source being applied to the pupil;
   a memory unit, wherein opioid pharmacokinetic data is stored within the memory unit;
   a processor in communication with the pupillometer and the memory unit, the processor including:
      a pharmacokinetic association module for associating the opioid pharmacokinetics with anticipated pupillary effects; and
      a respiratory depression prediction module for predicting a probability of opioid-related respiratory depression by comparing the anticipated pupillary effects from the pharmacokinetic association module and the detected pupillary effects from the pupillometer; and
   a user interface in communication with the processor, the user interface configured to provide the prediction of the probability of opioid-related respiratory depression from the respiratory depression prediction module to a user.

2. The quantitative pupillometry system of claim 1, wherein the memory unit processes the opioid pharmacokinetic data.

3. The quantitative pupillometry system of claim 1, wherein the image acquisition device comprises a charge-coupled device (CCD) camera, and the stimulus light source comprises an infrared light source.

4. The quantitative pupillometry system of claim 1, wherein the pupillary effects detected include at least one of a resting pupil diameter, a maximum pupil constriction velocity, an average pupil constriction velocity, a minimum diameter, a constriction amplitude, or a relaxation velocity.

5. The quantitative pupillometry system of claim 1, wherein the respiratory depression prediction module predicts the probability of opioid related respiratory depression based upon at least one of a difference of pupillary constriction over time, a difference of pupillary average constriction velocity over time, a difference of maximum constriction velocity over time, or a difference of pupillary size recovery over time.

6. The quantitative pupillometry system of claim 5, wherein the difference of pupillary constriction over time is between a measure at the end of surgery and a baseline measure.

7. The quantitative pupillometry system of claim 6, wherein the baseline measure is taken before surgery.

8. The quantitative pupillometry system of claim 5, wherein the difference of pupillary average constriction velocity over time is between a measure at 3 minutes after opioid is administered to the patient and a baseline measure.

9. The quantitative pupillometry system of claim 5, wherein the difference of maximum constriction velocity over time is between a measure at 3 minutes after opioid is administered to the patient and a baseline measure.

10. The quantitative pupillometry system of claim 5, wherein the difference of maximum constriction velocity over time is between a measure at postoperative care and a baseline measure.

11. The quantitative pupillometry system of claim 5, wherein the difference of pupillary size recovery over time is between a measure at postoperative care and a baseline measure.

12. A quantitative pupillometry system for predicting a probability of at least one opioid-related central effect comprising:
- a pupillometer including an image acquisition device and a stimulus light source, the image acquisition device configured to detect pupillary effects from a pupil of a patient in response to light from the stimulus light source being applied to the pupil;
- a processor in communication with the pupillometer, the processor including an opioid-related central effect prediction module for predicting a probability of at least one opioid-related central effect in response to the pupillary effects detected by the pupillometer, wherein the at least one opioid-related central effect includes respiratory depression, sedation or vomiting;
- a memory storing opioid pharmacokinetic data;
- the processor including a pharmacokinetic association module for associating the opioid pharmacokinetic data with the detected pupillary effects; and
- a user interface in communication with the processor, the user interface configured to display the prediction of the probability of the at least one opioid-related central effect from the processor to a user.

13. The quantitative pupillometry system of claim 12, wherein the image acquisition device comprises a charge-coupled device (CCD) camera, and the stimulus light source comprises an infrared light source.

14. The quantitative pupillometry system of claim 12, wherein the pupillary effects detected include at least one of a resting pupil diameter, a maximum pupil constriction velocity, an average pupil constriction velocity, a minimum diameter, a constriction amplitude, and a relaxation velocity.

15. The quantitative pupillometry system of claim 12, wherein the opioid-related central effect prediction module predicts the probability of at least one opioid-related central effect based upon at least one of a difference of pupillary constriction over time, a difference of pupillary average constriction velocity over time, a difference of maximum constriction velocity over time, or a difference of pupillary size recovery over time.

16. A method of predicting a probability of at least one opioid-related central effect comprising:
- administering an opioid to a patient;
- providing a pupillometer including a stimulus light source and an image acquisition device;
- stimulating a pupil of the patient via the stimulus light source of the pupillometer;
- acquiring an image of the stimulated pupil via the image acquisition device of the pupillometer;
- detecting pupillary effects of the pupil via the image acquisition device of the pupillometer;
- providing a processor in communication with the pupillometer, the processor including an opioid-related respiratory depression prediction module and a pharmacokinetic association module;
- providing a memory storing opioid pharmacokinetic data;
- associating, via the pharmacokinetic association module, the opioid pharmacokinetic data with anticipated pupillary effects;
- predicting, via the opioid-related respiratory depression prediction module of the processor, a probability of opioid-related respiratory depression by comparing the anticipated the anticipated pupillary effects from the pharmacokinetic association module and the detected pupillary effects from the pupillometer; and
- providing the predicted probability of the at least one opioid-related respiratory depression to a user by displaying the predicted probability of the at least one opioid-related respiratory depression on a user interface.

17. The method of claim 16, wherein the step of predicting the probability of the at least one opioid-related central effect is based upon one of a difference of pupillary constriction over time, a difference of pupillary average constriction velocity over time, a difference of maximum constriction velocity over time, and a difference of pupillary size recovery over time.

* * * * *